(12) United States Patent
Heacock et al.

(10) Patent No.: US 7,892,268 B2
(45) Date of Patent: Feb. 22, 2011

(54) PDT APPARATUS WITH HIGH OUTPUT LED FOR THERAPY AND AIMING

(75) Inventors: Gregory Lee Heacock, Auburn, WA (US); Wes Alan Williams, Silverdale, WA (US); William Louis Barnard, Maple Valley, WA (US); Wayde Hampton Watters, Kent, WA (US); Erik Ross Haugaard, Seattle, WA (US)

(73) Assignee: Light Sciences Oncology, Inc., Snoqualmie, WA (US)

( * ) Notice: Subject to any disclaimer, the term of this patent is extended or adjusted under 35 U.S.C. 154(b) by 1371 days.

(21) Appl. No.: 11/387,479

(22) Filed: Mar. 23, 2006

(65) Prior Publication Data

US 2007/0225777 A1 Sep. 27, 2007

(51) Int. Cl.
*A61N 5/06* (2006.01)
(52) U.S. Cl. ............................. 607/88; 606/2; 606/19; 607/95
(58) Field of Classification Search .............. 606/2–19; 607/88–95
See application file for complete search history.

(56) References Cited

U.S. PATENT DOCUMENTS

| 3,832,028 | A | * | 8/1974 | Kapron ..................... 385/43 |
| 6,033,431 | A | * | 3/2000 | Segal ......................... 607/89 |
| 6,319,273 | B1 | | 11/2001 | Chen et al. |
| 6,359,684 | B2 | * | 3/2002 | Ikezawa et al. ............. 356/124 |
| 6,486,499 | B1 | * | 11/2002 | Krames et al. ............... 257/81 |
| 7,001,413 | B2 | * | 2/2006 | Butler ........................ 607/88 |
| 2003/0125718 | A1 | * | 7/2003 | Munnerlyn et al. ........... 606/5 |
| 2004/0251469 | A1 | * | 12/2004 | Yatsuda et al. .............. 257/100 |
| 2005/0196720 | A1 | * | 9/2005 | Ostler et al. ................ 433/29 |
| 2005/0242362 | A1 | * | 11/2005 | Shimizu et al. .............. 257/99 |

* cited by examiner

*Primary Examiner*—Ahmed M Farah
*Assistant Examiner*—Aaron Roane
(74) *Attorney, Agent, or Firm*—McAndrews, Held & Malloy, Ltd.

(57) ABSTRACT

An apparatus for directing light to an eye for exciting a photosensitizer includes a high output or super bright LED and an optic that receives light from the LED and concentrates the light so that it is nearly collimated. The LED is a single light source that is used for both therapy and for diagnostics or aiming.

24 Claims, 3 Drawing Sheets

PDT APPARATUS WITH HIGH OUTPUT LED FOR THERAPY AND AIMING

CROSS-REFERENCE TO RELATED APPLICATIONS

N/A

STATEMENT REGARDING FEDERALLY SPONSORED RESEARCH OR DEVELOPMENT

N/A

TECHNICAL FIELD

The present invention relates to an apparatus for directing light to an eye for exciting a photosensitizing agent or photosensitizer to provide therapy for an ocular disease and more particularly, to such an apparatus that includes a high output or super bright LED and an optic that receives light from the LED and concentrates the light so that it is nearly collimated. The LED of the present invention is a single light source that is used both for therapy and for diagnostics or aiming.

BACKGROUND OF THE INVENTION

Photodynamic Therapy (PDT) is a known process in which light of a specific wavelength or waveband is directed to tissues undergoing treatment or investigation that have been rendered photosensitive through the administration of a photo-reactive or photosensitizing agent called a photosensitizer. In this therapy, a photosensitizer having a characteristic light absorption waveband is first administered to the patient, typically either orally or by injection or even by local delivery to the treatment site. Proliferating cells, such as those involved in many eye diseases, may preferentially take up or absorb a number of photosensitizers. Once the drug or photosensitizer has been administered and reaches the target tissue, the tissue is illuminated with light of an appropriate wavelength or waveband corresponding to the absorption wavelength or waveband of the photosensitizer.

The object of the PDT may be diagnostic, where the energy level and wavelengths of light are selected to cause the photosensitizer to fluoresce, thus yielding information about the tissue without damaging the tissue. The object of the PDT may also be therapeutic, where the wavelength of light delivered to the photosensitive tissue under treatment causes the photosensitizer to undergo a photo chemical interaction with oxygen in the tissue under treatment yielding free radical species such as a singlet oxygen, causing local tissue affect.

Typically, the light source used to excite the photosensitizer in PDT is a laser. However, the laser equipment used for PDT is relatively expensive. As an alternative, a non-coherent light source, such as an LED, has been used in PDT as described in U.S. Pat. No. 6,319,273. A typical LED, however, has a limited light output on the order of 350 mW. Moreover, because the LED light is non-coherent, a typical emission angle of a LED used in PDT is 180°. As a result, it is difficult to direct the light output from an LED to the eye without significant light loss.

BRIEF SUMMARY OF THE INVENTION

In accordance with the present invention, the disadvantages of prior PDT systems and apparatus for treating or diagnosing ocular diseases have been overcome. In accordance with the present invention, the PDT apparatus includes a high output or super bright LED and an optic that receives light from the LED and concentrates the light so that it is nearly collimated.

In accordance with one embodiment of the present invention, the PDT apparatus includes a LED having a light output that is greater than or equal to 700 mW, and preferably greater than or equal to 800 mW, when driven with a current to provide therapy light having a first wavelength for exciting a photosensitizer to provide therapy. A compound parabolic concentrator having an acceptance angle that is less than or equal to 30° receives light from the LED and directs light out with a much smaller emission angle than the emission angle of the LED.

In accordance with one feature of the present invention, the high output LED includes a top metallization grid with at least four wirebonds that are disposed at the corners of the metallization grid. The increased number of wirebonds improves current spreading so that the LED can be driven by a high current before roll off occurs. The position of the wirebonds at the corners of the metallization grid, which also corresponds to the corners of the LED die, ensures that the wirebonds block as little light as possible.

In accordance with a further feature of the present invention, the LED utilizes a passive heat removal system that consists of a heat spreader and a heat exchanger. A small electric fan may also be used to force air across the heat sink and improve heat transfer from the sink to the ambient environment. This passive heat removal system allows the apparatus of the present invention to provide a maximized light output with a constant wavelength, without the need of a costly active heating/cooling mechanism such as a thermal electric cooler (TEC).

In accordance with a further feature of the present invention, a wavelength selection filter is provided which is movable into the optical path of the LED light wherein the filter allows only light of a wavelength that will not excite the photosensitizer to provide therapy to pass so that the light may be used for diagnostic purposes or to form an aiming beam. After the aiming beam of light from the LED is used by a physician to target a particular area of diseased tissue in the eye, the filter may be moved out of the optical path of the LED light so that light of the therapy wavelength can be used to treat the diseased tissue.

In one embodiment of the present invention, when the wavelength selection filter is in position to provide the aiming beam of light, the LED is driven with less current than the current used to drive the LED when providing therapy light.

In accordance with a further feature of the present invention, the size and shape of the light directed to the eye is selected by an aperture wheel that includes a number of different sized apertures. The aperture wheel may be rotated to position a selected aperture in the path of the LED light so as to control the size and/or shape of the light used for therapy.

These and other advantages and novel features of the present invention, as well as details of an illustrated embodiment thereof, will be more fully understood from the following description and drawings.

DETAILED DESCRIPTION OF THE INVENTION

An apparatus 10 in accordance with the present invention directs light to a patient's eye for photodynamic therapy or diagnostics. The apparatus 10 includes a super bright LED 12, as discussed in detailed below, with a light output greater than 700 mW and preferably greater than 800 mW. The LED 12 is mounted on a heat spreader 14 that is in turn mounted on a heat sink heat exchanger 16. The heat spreader 14 and the heat sink 16 provide a passive heat removal system for the LED 12 to maintain the LED wavelength constant as discussed below. Light from the LED 12 is received by a compound parabolic concentrator (CPC) 18 to provide nearly collimated light output from the CPC 18.

Figure 6:
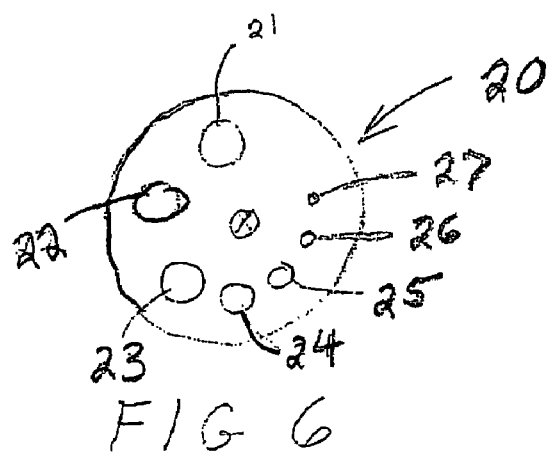
FIG. 6 is a top view of an aperture wheel in accordance with the present invention.

The size of the light used for PDT can be controlled by an aperture wheel 20 shown in greater detail in FIG. 6. The aperture wheel is a rotatable disk that has a number of apertures 21-27 of different sizes that are spaced above the wheel 20. The wheel 20 can be rotated to position a selected aperture 21-27 in the path of light from the CPC 18 such that it over fills the largest aperture 21 of the wheel 20. The diameter of the beam of light as it exits the selected aperture 21-27 is equal to the diameter of the selected aperture. Thus, by positioning different apertures 21-27 in the path of light from the CPC 18, the size of the light can be controlled. Although each of the apertures 21-27, as shown in FIG. 6, is circular in shape, the wheel 20 can be formed with apertures of different shapes as well. In this way, both the size and the shape of the light being used for PDT can be selected and controlled by the physician.

A movable wavelength selection filter 30 can be moved into or out of the path of the LED light so as to allow a single light source, in this case the LED 12, to be used as both the therapy light and an aiming beam. For example, when the photosensitizer is talaporphin sodium, the center wavelength of light for exciting the photosensitizer to provide therapy for diseased tissue is preferably 664 nm. As such, the LED 12 is designed to emit light having a constant center wavelength of 664 nm when driven with a high current, as discussed below. In order to produce the aiming beam from the LED 12, the current driving the LED 12 is reduced to cause a downward shift in the center wavelength of the LED light and the filter 30 is moved into the path of the LED light. The filter 30 is such that it passes a waveband of light that will not excite the photosensitizer for therapy, but the waveband of light will cause the photosensitizer to fluoresce so that the light can be used for diagnostic purposes or as an aiming beam. When the photosensitizer is talaporphin sodium, the preferred center wavelength of the aiming beam is 635 nm. After the physician uses the aiming beam to target the tissue to be treated, the filter 30 is moved out of the path of the LED light so that light having the therapy wavelength can be directed to the targeted tissue.

The LED light passing through the selected aperture of the aperture wheel 20 is collected by a collector lens 34. The light from the collector lens 34 passes through a pair of relay lenses 36 to a safety filter mirror 38. The mirror 38 is a reflector that reflects the LED light out of the apparatus 10 to the patient's eye 42. In a preferred embodiment, the apparatus 10 is used in conjunction with a contact lens 40 which may be a Meinster high magnification contact lens from Ocular. The safety filter mirror 38 is such that it blocks therapy light reflected from the patients eye 42 from reaching viewing optics 44 which allow a physician 46 to view the interior of the patient's eye and thus the tissue being treated. However, the safety filter mirror 38 allows light having the aiming beam wavelength that is reflected from the eye to pass through to the viewing optics 44 so as to allow a physician 46 to view the targeted tissue. In a preferred embodiment, the mirror 38 is preferably rotatable by the doctor so that the doctor can position the aiming beam so that it impinges on the desired targeted tissue. Once the aiming beam is correctly positioned by the physician on the targeted tissue, the filter 30 can be moved out of the LED light path and the current driving the LED 12 increased to provide the therapy light to the targeted eye tissue.

The high output of the super bright LED 12 on the order of 700 mW or greater and preferably 800 mW or greater is achieved by a combination of factors. These factors include a top metallization configuration for the LED die that provides improved current spreading while minimizing the light blocked by the metallization grid. Other factors include designing the LED to account for the wavelength shift that occurs when the LED is driven from low currents up to the maximum drive current of the LED. In a preferred embodiment the LED is also driven to provide the therapy wavelength of light with a current that is near the point at which roll off occurs. A further factor in achieving the high light output of the LED while maintaining a constant wavelength is the passive heat removal system for the LED 12.

As background for the present invention, it should be appreciated that the peak wavelengths of a typical LED can vary by ±10 nm or more. However, for PDT applications spectral control is very important. The PDT effect can be modeled as the absorption spectrum of the photosensitizer with the illumination light spectrum. The larger the convolution result, the greater the PDT effect and the more efficient the drug/light system operates. Increased PDT efficiency allows for the use of less drug which reduces the possibility of undesired side effects. Increased PDT efficiency can also reduce the demands on the light delivery apparatus. This in turn reduces cost and increases safety since the light output is less powerful. It is important to realize that as the junction temperature of the LED increases, the wavelength spectrum "red-shifts." For example, a typical LED may have a center wavelength of 660 nm at 39° whereas the center wavelength of that LED will shift to 665 nm at 63°. Further, as the junction temperature of the LED increases the light output of the LED decreases. Thus, one of the keys to a high optical output is good thermal management since the cooler the LED junction can be kept, the more output photons are produced for the same electrical input or drive current. If the heat could be 100% instantaneously removed, then increasing the drive current to the LED would result in a linear increase in the light output by the LED. In the real world, this happens up to a limit and then the light output of the LED rolls off. Eventually, an increase in drive current actually results in less light output. It is at this point that the LED has been damaged by a drive current that is too high. The traditional approach to obtaining a given light output at a constant peak or center wavelength is to use an active heating/cooling mechanism such as a thermal electric cooler (TEC). The TEC is used to add or remove heat depending on how much "self-heating" from electric resistance heating is going on. The more drive current, the more self-heating that occurs and the more red-shift in the wavelength occurs. This is then balanced with either less TEC heating or TEC cooling to remove the heat.

In accordance with the present, a maximized light output at a constant and specific light frequency has been attained for the LED 12 in a manner that reduces and eliminates the need for a TEC. In accordance with one feature of the present invention, a passive heat removal system is provided for the LED 12 via the heat spreader 14 and the heat sink 16 on which the LED 12 is mounted. In a preferred embodiment, the heat spreader 14 is a copper plate having a 50-100 micro inches nickel diffusion layer and a 50 micro inches layer of 24 carat gold. In a preferred embodiment, the LED die is secured to the heat spreader 14 with a silver filled epoxy so as to provide a very fine or thin layer of silver particles between the die and the heat spreader. The silver filled epoxy is selected because it has good thermal conductivity. The heat sink 16 may be a conventional heat sink having a plurality of fins or the like. Further, in a preferred embodiment, a small electric fan can be used to force air across the heat sink 16 and improve the heat transfer from the heat sink to the ambient environment.

In order to provide the high output LED, the doping chemistry of the LED die 12 is preferably chosen to account for the natural red-shift that occurs as the LED heats up. For example, the wavelength of the LED 12 shifts up by about 8-10 nm when the drive current is changed from the lowest current to the maximum drive current. Thus, the LED die chemistry is selected to provide 655 nm under low drive current conditions and to provide a wavelength of 664 nm for therapy when driven with the higher driving current. The current used to drive the LED to provide the therapy light is preferably near the point at which roll off occurs to provide the maximum light output. The drive current may also be as high as the point at which roll off occurs in one embodiment where the LED 12 is used once per therapy. Because the LED 12 is not turned on for lengthy periods of time, the present invention takes advantage of the trade off between the life cycle of the LED and the drive current. That is, the LED is driven at higher currents with the trade off being a shorter lifetime.

Figure 1:
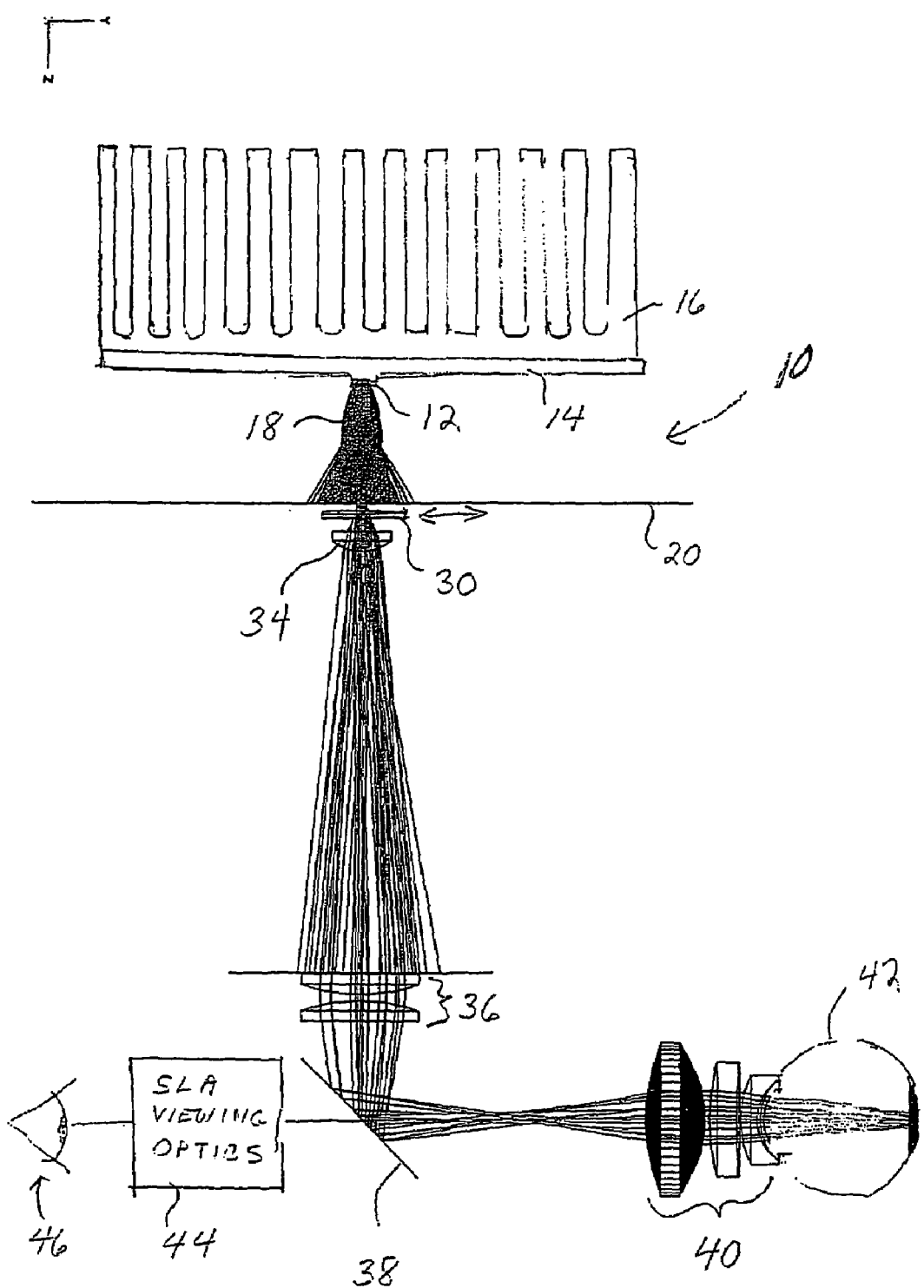
FIG. 1 is an illustration of the optical system of the apparatus of the present invention for directing therapeutic and aiming light to a patient's eye.
Figure 2:
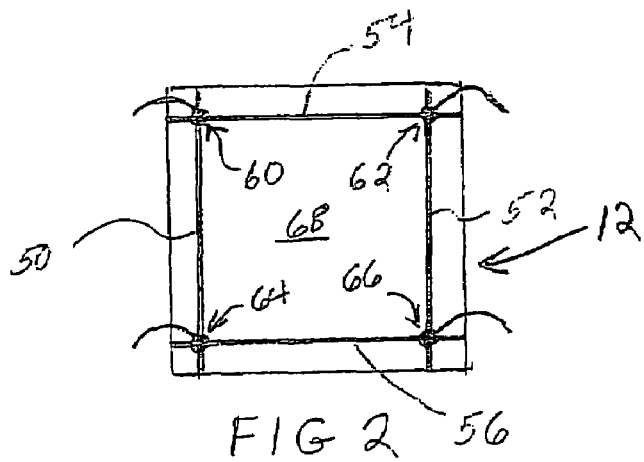
FIG. 2 is a top view of an LED die having a metallization grid and at least four wirebonds in accordance with the present invention.

In accordance with another feature of the present invention, the extremely high light output of the LED 12 on the order of 700 mW or greater and preferably 800 mW or greater is provided by an improved top metallization layer for the LED die. This metallization layer is depicted in FIG. 2. The top metallization layer of the LED die 12 includes metalized lines 50 and 52 that are parallel to each other. The LED die 12 also includes metalized lines 54 and 56 which are parallel to each other where the parallel lines 50 and 52 intersect the parallel lines 54 and 56 to form a metalized grid. In a preferred embodiment, the lines 50 and 52 are perpendicular to the lines 54 and 56 so as to provide a square or rectangular grid pattern with the intersection points located hear the corners of the LED die 12. To increase the light output of the LED 12, the number of wirebonds for the LED die 12 is increased from the typical number of two wirebonds to four wirebonds 60, 62, 64 and 66 located at the intersections of the metallization lines. The increased number of wirebonds improves current spreading so that the LED can be driven by higher currents before roll off occurs to provide a higher light output. By locating the wirebonds 60, 62, 64 and 66 at the corners of the LED die 12, the central active area 68 of the LED die is increased with minimal blocking of the light output by the wirebonds 60, 62, 64 and 66. The preferred embodiment of the LED die 12 includes four wirebonds for a 1 mm×1 mm square LED, although the size of the LED may be increased to 1.5 mm².

Figure 3:
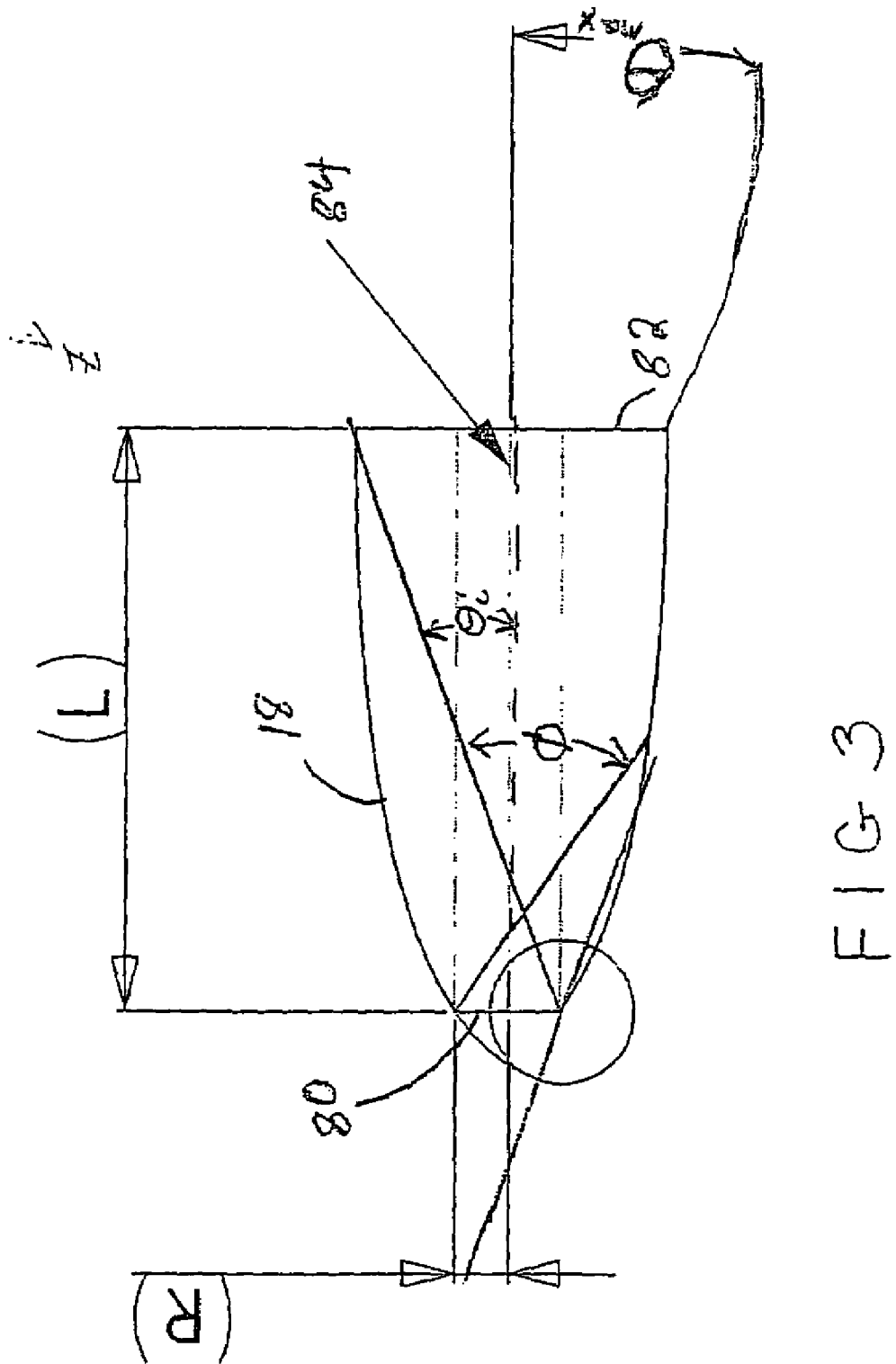
FIG. 3 is an illustration of the compound parabolic concentrator of the present invention.

The compound parabolic concentrator (CPC) 18 is shown in greater detail in FIG. 3. The CPC 18 is a solid optical element with a refractive index n in the range of 1.3-2.0 and preferably 1.5. The CPC has a first optical surface or aperture 80 for receiving light from the LED 12 wherein the light exits the CPC 18 through a second surface or optical aperture 82 such that the light is nearly collimated. The radius R of the first surface 80 of the CPC 18 is preferably between 0.5 mm to 2.0 mm. The exit angle $\theta_{max}$ is preferably between 5° to 30° so that the light that exits the CPC 18 is nearly collimated. The CPC 18 surface of revolution about the Z axis is defined by the following form equations.

$$L = \frac{R(1 + \operatorname{Sin}\theta_i)\operatorname{COS}\theta_i}{\operatorname{Sin}^2\theta_i} \quad \text{(eq. 1)}$$

$$\theta_i = \frac{\theta_{max}}{n} \quad \text{(eq. 2)}$$

$$R = \frac{2R(1 + \operatorname{Sin}\theta_i)\operatorname{Sin}(\phi - \theta_i)}{1 - \operatorname{COS}\phi} - R \quad \text{(eq. 3)}$$

$$Z = \frac{2R(1 + \operatorname{Sin}\theta_i)\operatorname{COS}(\phi - \theta_i)}{1 - \operatorname{COS}\phi} \quad \text{(eq. 4)}$$

Figure 4:
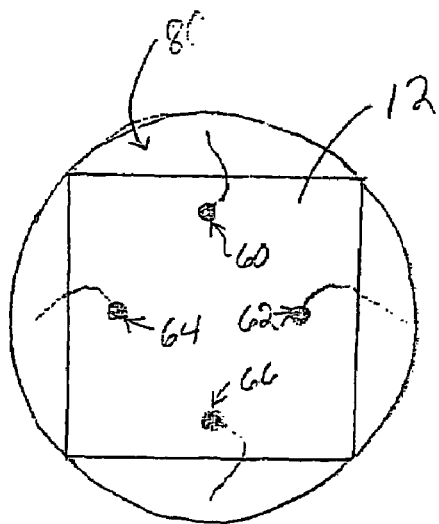
FIG. 4 is an illustration of the position of the wirebonds on the LED die with respect to the aperture of the compound parabolic concentrator on which the die is mounted in accordance with one feature of the present invention.
Figure 5:
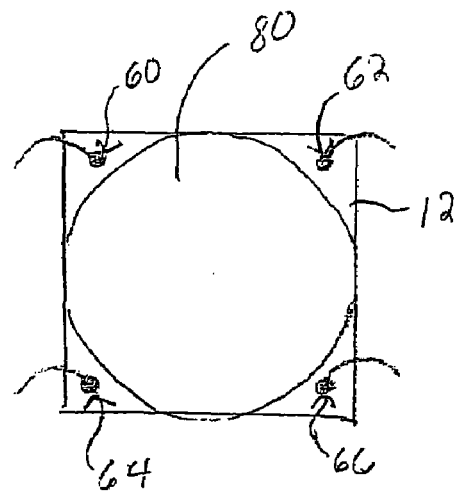
FIG. 5. is an illustration of the position of the wirebonds on the LED die with respect to the aperture of the compound parabolic concentrator on which the die is mounted in accordance with another embodiment of the present invention.

In a preferred embodiment, the LED die 12 is mounted on the surface 80 of the CPC 18 using an index matching silicone gel that couples the die 12 to the CPC. In one embodiment, as shown in FIG. 4, the LED die 12 is smaller than the surface 80 of the CPC 18 such that when the LED die is mounted on the CPC 18, the square LED die 12 forms a square within the circular surface 80 of the CPC 18. In this embodiment the maximum amount of light from the LED is received by the CPC 18. In another embodiment depicted in FIG. 5, the circular surface 80 of the CPC 18 is contained within the square surface of the die 12 so that the wirebonds 60, 62, 64 and 66 are not between the surface 80 of the CPC 12 and the area of the LED die 12 contacted by the CPC 18 when the LED is mounted on the CPC 18. In this embodiment substantially all of the light from the LED is received by the CPC 18 but the wirebonds do not interfere with the coupling between the LED and CPC. Further, to maximize the light from the LED received by the CPC 18, the diameter of the surface 80 of the CPC 18 is preferably equal to or close to the height and/or width of the LED die 12 as shown in FIG. 5.

The apparatus of the present invention for directing light to an eye for PDT uses a super bright LED with a constant therapy wavelength so that a lower dosage of the photosensitizer drug is needed, thereby reducing the possibility of undesirable side effects. Moreover, the same LED used for therapy may be used to provide an aiming beam or diagnostic light to the eye without causing any therapy effect by merely lowering the drive current to the LED and moving the wavelength selection filter 30 into place. The new CPC of the present invention outputs nearly collimated light from the LED so as to substantially increase the percentage of light from the LED that is directed into the patient's eye. Many modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. An apparatus for directing light to an eye for exciting a photosensitizer comprising:
   a LED having a light output greater than or equal to 700 mW when driven with a current to provide therapy light having a first wavelength for exciting the photosensitizer to provide therapy;
   a compound parabolic concentrator having an acceptance angle that is less than or equal to 30°, the compound parabolic concentrator receiving light from the LED and directing light out with a smaller emission angle than the emission angle of the LED;
   one or more optics for receiving light from the compound parabolic concentrator and directing the light out of the apparatus; and
   a filter movable into the optical path of the LED light, the filter allowing a second wavelength of light to pass that will not excite the photosensitizer to provide therapy, the second wavelength of light providing diagnostic light or an aiming beam.

2. An apparatus as recited in claim 1 wherein the LED has a 1 mm$^2$ to 1.5 mm$^2$ die.

3. An apparatus as recited in claim 1 wherein a die of the LED has a top metallization grid with at least four wirebonds.

4. An apparatus as recited in claim 3 wherein the four wirebonds are disposed near the corners of the metallization grid.

5. An apparatus as recited in claim 4 wherein the metallization grid has a first metalized line in parallel with a second metalized line and a third metalized line in parallel with a fourth metalized line wherein the first and second metalized lines intersect the third and fourth metalized lines at intersection points and the wirebonds are located at the intersection points.

6. An apparatus as recited in claim 1 wherein the light output of the LED is greater than or equal to 800 mW.

7. An apparatus as recited in claim 1 wherein the LED can be driven by at least 2 amps of current before current roll over occurs.

8. An apparatus as recited in claim 1 wherein the LED is mounted on a heat spreader.

9. An apparatus as recited in claim 8 wherein the heat spreader is plated with nickel and gold.

10. An apparatus as recited in claim 8 wherein the LED is secured to the heat spreader with a metal filled epoxy.

11. An apparatus as recited in claim 10 wherein the metal filled epoxy is a silver filled epoxy.

12. An apparatus as recited in claim 8 wherein the heat spreader is mounted on a heat sink.

13. An apparatus as recited in claim 1 wherein the LED is mounted on a passive heat removal system.

14. An apparatus as recited in claim 13 wherein the passive heat removal system includes a heat spreader and heat sink.

15. An apparatus as recited in claim 14 wherein the passive heat removal system includes an electric fan.

16. An apparatus as recited in claim 1 wherein the compound parabolic concentrator has a first surface for receiving light and a second surface through which light exits, the first surface being smaller than the second surface and wherein the LED is mounted on the first surface.

17. An apparatus as recited in claim 16 wherein the LED has at least four wirebonds that are located outside of the first surface of the compound parabolic concentrator.

18. An apparatus as recited in claim 16 wherein the LED is secured to the compound parabolic concentrator with an index matching silicon gel.

19. An apparatus as recited in claim 1 wherein the compound parabolic concentrator has a first surface for receiving light from the LED, the first surface having a radius of 0.5 mm to 2.0 mm.

20. An apparatus as recited in claim 1 wherein the therapy light has a center wavelength of approximately 664 nm and the diagnostic light or aiming beam has a center wavelength of approximately 635 nm.

21. An apparatus as recited in claim 1 wherein the LED is driven by a current and is driven with less current when the LED is used to provide the diagnostic light or aiming beam than the current used to drive the LED when providing therapy light.

22. An apparatus as recited in claim 1 wherein the optics for receiving light from the parabolic concentrator include a selective reflector that reflects light of the first and second wavelength towards an eye of a patient and that passes light of the second wavelength reflected from a patient's eye to optics to allow a user to see what eye tissue the aiming beam is impinging on, the selective reflector blocking light of the first wavelength that is reflected from the patient's eye.

23. An apparatus as recited in claim 1 including a member having a plurality of selectable apertures of different sizes, the member being movable to position one of the apertures in the path of the LED light to control the size of the light used for therapy.

24. An apparatus as recited in claim 1 wherein the member is a disk that is rotatable to position different apertures in the path of the LED light.

* * * * *